United States Patent [19]
Lieberman

[11] Patent Number: 5,290,301
[45] Date of Patent: Mar. 1, 1994

[54] CAM GUIDED CORNEAL TREPHINE

[76] Inventor: David M. Lieberman, 300 E. 51st St., Apt. 18B, New York, N.Y. 10022

[21] Appl. No.: 773,839

[22] Filed: Oct. 9, 1991

[51] Int. Cl.⁵ ............................................. A61B 17/32
[52] U.S. Cl. .................................... 606/166; 606/180
[58] Field of Search ............................ 606/166, 180

[56] References Cited

U.S. PATENT DOCUMENTS

| | | | |
|---|---|---|---|
| 2,249,906 | 7/1941 | Longoria | 128/303 |
| 3,537,345 | 11/1970 | Luppino | 83/12 |
| 3,628,522 | 12/1971 | Kato | 128/305 |
| 4,085,508 | 4/1978 | Gyongyosi | 33/27 |
| 4,205,682 | 6/1980 | Crock et al. | 128/305 |
| 4,298,004 | 11/1981 | Schachar et al. | 128/305 |
| 4,342,951 | 8/1982 | Muller et al. | 318/625 |
| 4,417,579 | 11/1983 | Soloviev et al. | 128/303 |
| 4,423,728 | 1/1984 | Lieberman | 128/310 |
| 4,429,696 | 2/1984 | Hanna | 128/310 |
| 4,470,159 | 9/1984 | Peyman | 3/13 |
| 4,520,815 | 6/1985 | Marinoff | 128/303 |
| 4,526,171 | 7/1985 | Schachar | 128/305 |
| 4,593,467 | 6/1986 | Safar | 30/300 |
| 4,718,418 | 1/1988 | L'Esperance, Jr. | 128/303 |
| 4,807,623 | 2/1989 | Lieberman | 128/305 |
| 4,815,463 | 3/1989 | Hanna | 606/166 |
| 4,834,748 | 5/1989 | McDonald | 623/5 |

*Primary Examiner*—Edgar S. Burr
*Assistant Examiner*—John S. Hilten
*Attorney, Agent, or Firm*—Anthony J. Casella; Gerald E. Hespos

[57] ABSTRACT

A cam guided corneal trephine for selectively cutting a portion of an eye is provided herein. The cam-guided corneal trephine comprises a base, a coarse adjusting ring, interchangeable annular ring, interchangeable annular cams operatively supported by the adjusting ring, the annular cams having various inner round diameters or other than round dimensions, and a roller cage assembly adapted to be disposed and rotated within the annular cam, the roller cage assembly having a blade mounting means disposed therein for providing a continuous cut of the corneal tissue corresponding to the inner shape of the selected cam upon rotation of the roller cage assembly.

18 Claims, 4 Drawing Sheets

FIG. 1

CAM GUIDED CORNEAL TREPHINE

FIELD OF THE INVENTION

The present invention is directed to a cam guided corneal trephine used to cut a circular or non-circular (or other than round) portion of the cornea.

BACKGROUND OF THE INVENTION

Corneal trephines have been used in lamellar and penetrating keratoplasty. Originally, such trephines have been in the form of a honed cylinder as developed by Castroviejo. Many surgeons have attempted to improve the techniques as developed by Castroviejo, see U.S. Pat. No. 4,423,728. Many surgical companies have attempted to make holders for such cylinders in order to improve the visualization of the cutting edge but such attempts have generally been insufficient due to lack of proper centering, obscuration of the cutting edge at sometime during the procedure, independent eye and trephine movements, and lack of ability to cut other than round windows in the corneal tissue.

An improved corneal trephine was developed by David M. Lieberman, M.D., as described in the American Journal of Ophthalmology, May, 1976, pages 684–685. As described therein, the surgical instrument was comprised of inner and outer cones, the inner cone revolving within the outer cone. The outer cone included an upper ridge held by the non-dominant hand of the surgeon, stabilizing the instrument on the eye, and a lower ridge containing an annular suction device which firmly held the eye with a pressure of from 10-15 mm Hg to assure centration of the device over the cornea. The inner cone revolved within the outer cone and carried a slide mechanism with an attached disposable razor blade. To perform the incision, the inner cone which carried the blade was rotated about the cornea. After each rotation, the blade was lowered a few thousandths of an inch by turning a screw and the inner cone was rotated again. The incision could be viewed through an operating microscope. The slide mechanism upon which the blade was mounted was controlled by an adjustment screw for varying the radial position of the blade. Two interchangeable cutters could be used, one at a time. The first provided the razor blade at a 20° angle. The second cutter mechanism held the blade vertically and was suitable for keratoplasty in which a donor cornea had been punched for reinsertion onto a patient's cornea.

Although the single trephine described above represented a significant advance in the art, the device could only provide a round cut and, consequently, could not be employed whenever an other than round incision was required.

A second improved corneal trephine was developed by David M. Lieberman, M.D., and is disclosed and claimed in U.S. Pat. No. 4,423,728 which disclosure is hereby incorporated herein by reference. The advantages of this trephine include the use of a circular or non-circular cam which guides the path of the cutting blade to provide either a circular or other than round cut of the cornea. As described therein, the surgical trephine comprises a base, a non-circular cam guide operatively connected to the base, and a rotation cone adapted to be disposed and rotated on the base, the rotation cone having a blade mounting means provided thereon. The blade mounting means includes a slide mechanism with an attached disposable razor blade and is further provided with a slave wheel which rides on the non-circular cam guide such that upon rotation of the circular rotation cone the blade means provides a cut of the cornea following the pattern of the annular cam guide. The razor blade is connected to the blade mounting means through a vertical adjustment screw such that upon adjustment of the screw, the blade could be moved vertically to control the depth of cut of the blade into the corneal tissue.

The above device was also provided with an angled blade mounting means which operated similarly to the vertical blade means to provide a cut within the corneal tissue in an other than vertical manner.

And, while the cam-guided trephine device described above and in U.S. Pat. No. 4,423,728 represented a significant advance in the art over the single point trephine described in the David M. Lieberman article, the cam guided trephine could still be improved. Specifically, the razor blade had a tendency to wobble during rotation of the blade, and the depth of cut of the cornea was difficult to accurately control. Further, since the complete cutting action of the corneal tissue was interrupted after each rotation of the blade means to incrementally lower the cutting blades, the cornea lamella is allowed to spread providing an uneven incision or "hour-glass" effect. Further, the process of making a complete cut through the corneal tissue was very slow. And, further, the sudden incremental lowering of the cutting blade for each new rotation of the blade means tended to displace the corneal tissue and thereby producing an uneven cut.

SUMMARY OF THE INVENTION

It is therefore an object of the invention to provide a cam-guided corneal trephine which overcomes the disadvantages of the prior art trephines.

It is a further object to provide a cam-guided corneal trephine having an interchangeable blade means providing either a vertical or angled cut with respect to the corneal surface of the eye.

It is a further object of the invention to provide a cam-guided corneal trephine which includes a blade which can provide either a "round" or "other than round" cut of the cornea.

It is a further object of the invention to provide a cam-guided corneal trephine which includes a cutting blade and roller cage assembly that will decrease any wobble during rotation of the roller cage assembly within an interchangeable cam. The cams can have either an inner round cam guiding surface or an inner non-round cam guiding surface to allow the cutting blade to cut either a round or other than round hole in the corneal tissue.

It is a further object of the invention to provide a cam-guided corneal trephine which includes an inner adjusting ring which supports the roller cage assembly and cutting blade to provide a course blade height adjustment relative to the surface of the corneal tissue.

It is a further object of the invention to provide a cam-guided corneal trephine which includes a roller cage assembly supporting a cutting blade which provides a continuous cutting action during rotation of the roller cage assembly to provide a smooth, uninterrupted cut of the corneal tissue.

And, it is a further object of the invention to provide a cam-guided corneal trephine which includes a blade holding means supporting a cutting blade which continuously advances the cutting blade towards the corneal tissue of the eye during rotation of the blade holding means to provide a smooth uninterrupted cut of the corneal tissue without wobble or deflection of the cutting blade.

In accordance with the above objects, a novel cam-guided corneal trephine device is provided herein The cam-guided corneal trephine comprises a base, a course adjusting ring, interchangeable annular cams operatively supported by the adjusting ring, the annular cams having various inner round diameters or other than round dimensions, and a roller cage assembly adapted to be disposed and rotated within the annular cam, the roller cage assembly having a blade mounting means disposed therein for providing a cut of the corneal tissue corresponding to the inner shape of the selected cam upon rotation of the roller cage assembly.

The blade mounting means provides a continuous adjustment of the blade height or blade advancement upon rotation of the roller cage assembly while grasping the end of the blade mounting means. This continuous blade advancement is accomplished by use of a differential thread arrangement provided within the blade mounting means to allow the tip of the blade to advance downwardly 0.096 mm per revolution of the roller cage assembly and blade mounting means as is further described below.

More specifically, the roller cage assembly includes a generally circular cage having three rollers provided therein. A first roller is fixed within the cage and has the blade mounting means secured through its diameter. The other two rollers are affixed to the cage in radial slots and are biased outwardly from the cage to allow the roller assembly to be rotated about the inner cam surface. In this fashion the roller cage assembly can be rotated within a cam having an other than round inside dimension.

BRIEF DESCRIPTION OF THE DRAWINGS

The invention will be described in detail with reference to a preferred embodiment thereof, which is an ophthalmic cam-guided corneal trephine for performing a penetrating keratoplasty surgical operation. In the drawings:

FIG. 1 is a cross-sectional view of the cam-guided corneal trephine taken through section 1—1 of FIG. 2;

DETAILED DESCRIPTION OF THE INVENTION

Figure 1:
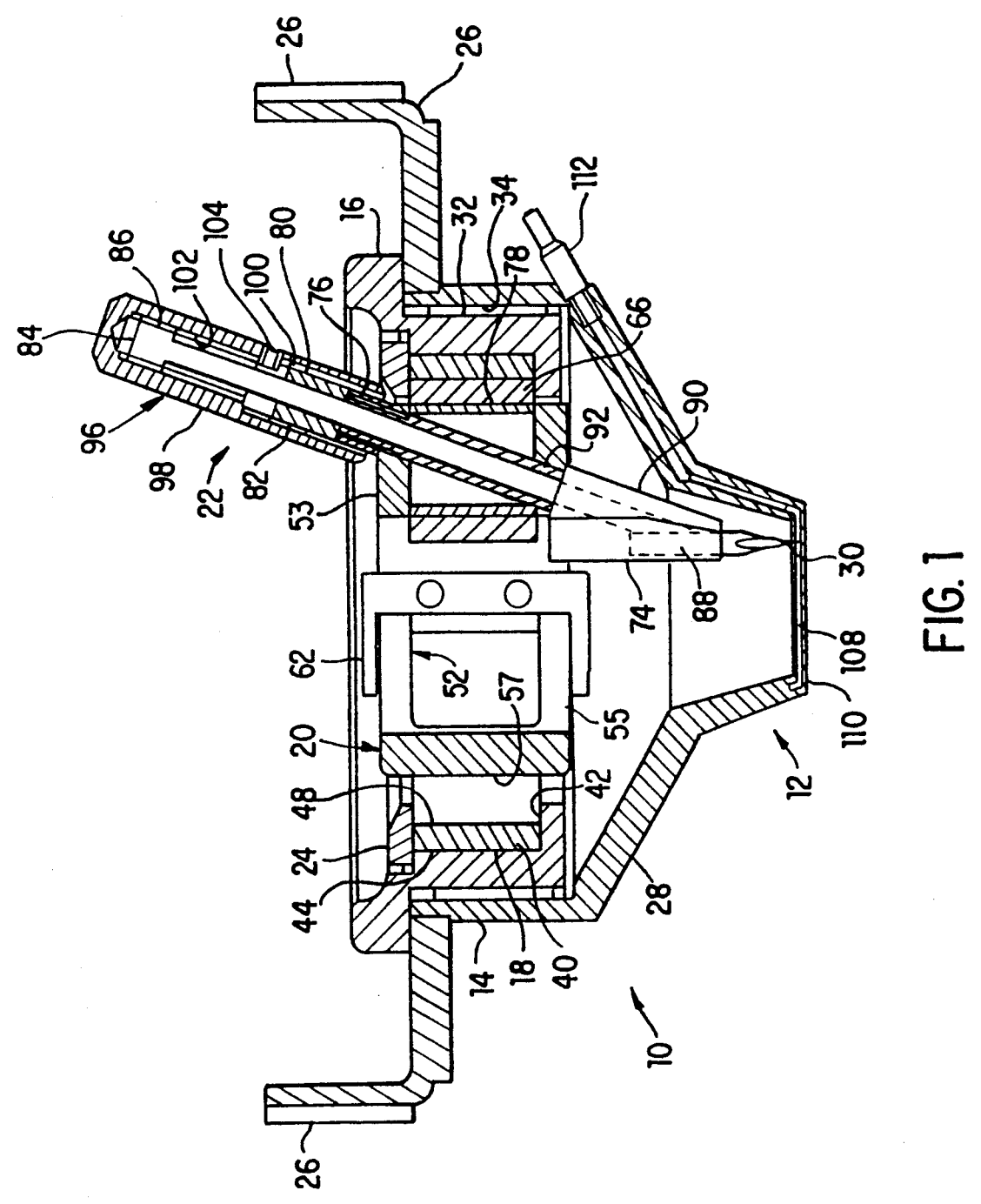
Figure 2:
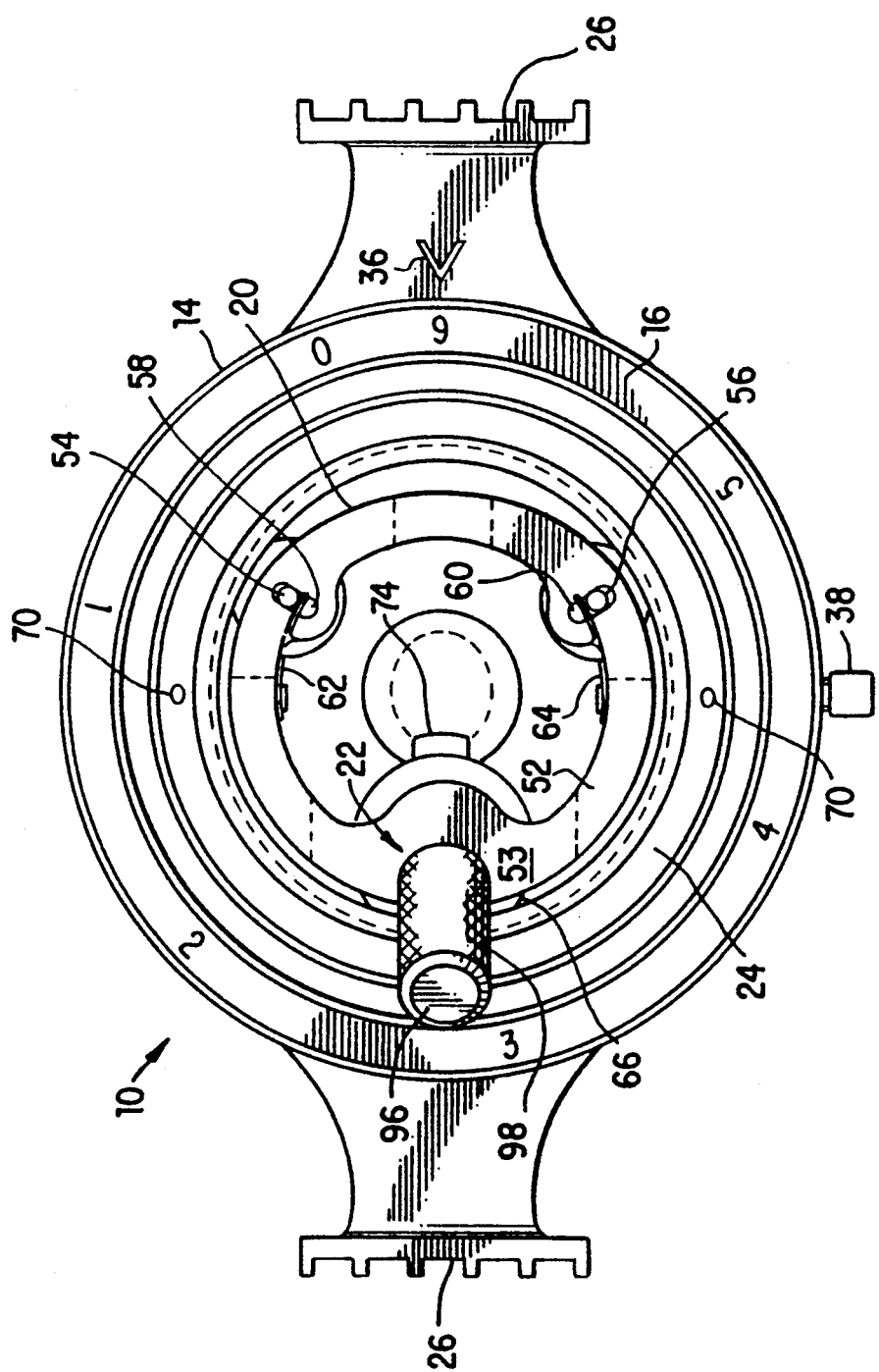
FIG. 2 is a top view of the cam-guided corneal trephine illustrated in FIG. 1.
Figure 3:
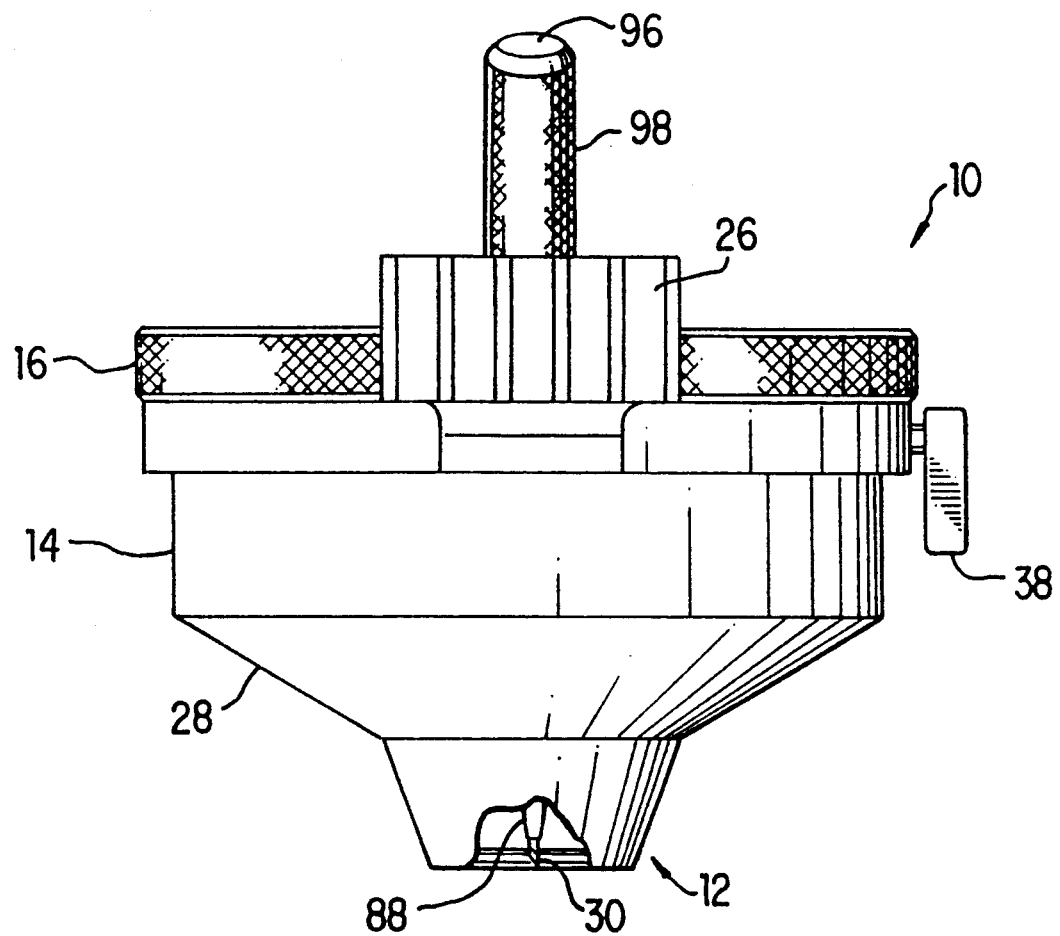
FIG. 3 is a side view of the cam-guided corneal trephine illustrated in FIG. 1.

The cam-guided corneal trephine according to the present invention is shown in FIGS. 1-5. Specifically referring to FIG. 1, the cam-guided corneal trephine 10 as shown includes a suction ring 12 for conforming and securing the patient's eye E and trephine 10, an annular base 14 integral with the suction ring 12, a course adjustment ring 16, an interchangeable cam 18, a roller cage assembly 20 and a blade mounting means 22 mounted within roller cage assembly 20 for rotational movement relative to the annular base 14 integral with the suction ring 12. A locking or retaining ring 24 is secured into the top of the adjustment ring 16 to secure the cam 18 and roller cage assembly 20 within the adjustment ring 16. The base 14 includes a pair of finger grips 26. In the device shown in the Figures, suction ring 12 and base 14 are connected by an outer cone 28, and elements 12, 14 and 28 are formed from a single integral piece. The blade mounting means 22 includes a moveable diamond tipped cutting blade 30 for cutting the corneal tissue.

The course adjustment ring 16 is provided with an external thread 32 which is received within a mating internal thread 34 provided in the annular base 14. The course adjustment ring 16 provides for a 6 millimeter (mm) adjustment of the blade mounting means 22 relative to the corneal surface of the eye E. The top surface of the adjustment ring 16 is provided with a plurality of number indicators 1 through 6 positioned about the periphery of the ring and the base is marked with a "V" as shown at 36 to provide a reference point for marking the position of the adjustment ring 16. The adjustment ring 16 is provided with a locking screw 38. The locking screw 38 is tipped with a nylon insert (not shown). When the course adjustment ring 16 is threaded into the base 14 such that the cutting blade 30 is positioned immediately adjacent the patient's cornea, the locking screw 38 is threaded through the ring 16 until the nylon tip is in contact with the external threads 32 of ring 16 to hold the ring in position relative to the annular base 14. In one embodiment of the invention by way of example and not to be construed in a limiting manner, the external thread 32 of ring 16 and internal thread 34 of base 14 are of a truncated metric thread design having a diameter of 47 mm and a pitch of 6.35.

Figure 4:
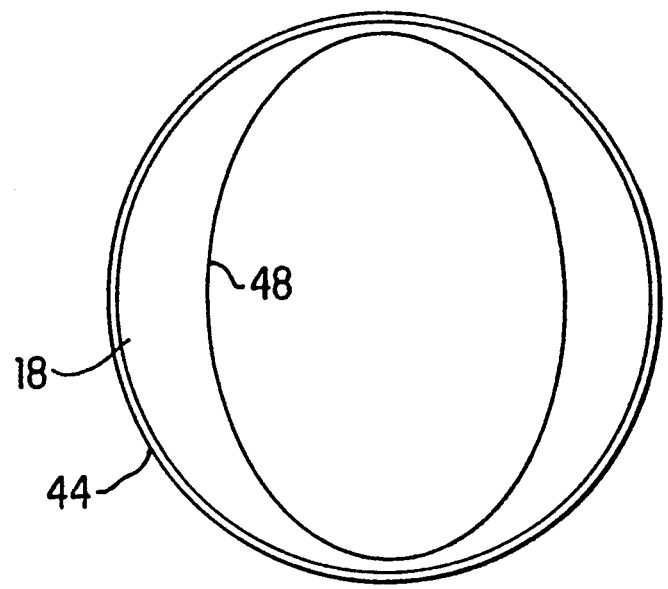
FIG. 4 is a top view of an other than round cam having a circular outer diameter and an annular or oval inside dimension.
Figure 5:
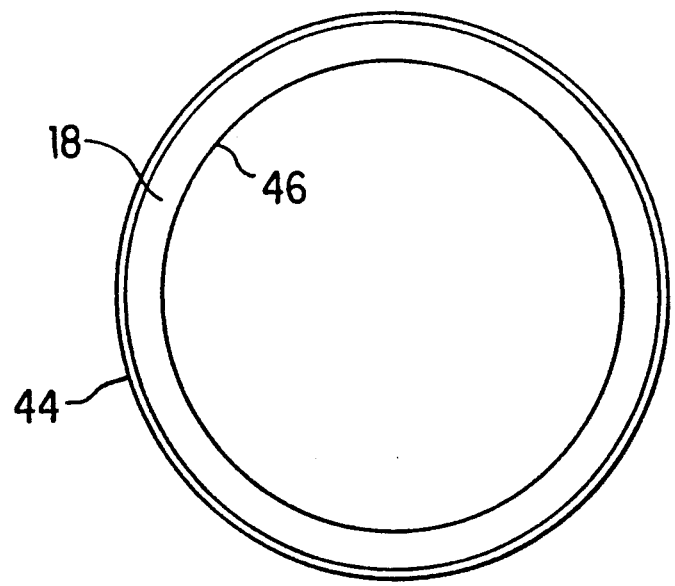
FIG. 5 is a top view of a totally round cam having both circular outer and inner diameters.

The adjustment ring 16 is provided with an inner circular surface 40 and a bottom bearing surface 42. The interchangeable cam 18 as shown in FIGS. 4 and 5 is positioned within the adjustment ring 16. The outer generally circular surface 44 of the cam 18 is configured to fit snugly against the inner surface 40 and is supported on the bottom bearing surface 42 of ring 16. The cam 18 is further held in position within ring 16 by use of a set screw (not shown). The inner surface of the cam 18 can either be configured in either a generally circular or round shape as shown at 46 in FIG. 5 or an other than round shape as shown at 48 in FIGS. 2 and 4.

The roller cage assembly 20 includes a cylindrical cage member 52 for supporting the blade mounting means 22 for rotational movement within the annular base 14 and ring 16. The cage member 52 includes a top member 53 with three depending cylindrical side members 57 and a bottom member 55 which can be affixed to the depending side members 57 to form an integral cage member 52. The cage assembly is provided with three (3) rollers positioned about the periphery of cage member 52 at approximately 120° from one another. Two of the rollers 54 and 56 are spring loaded and are received in radial slots 58 and 60, respectively provided in top and bottom surfaces 53 and 55, respectively on cage member 52. The spring loaded rollers 54 and 56 are biased radially outwardly from the cage member 52 by springs 62 and 64, respectively. A third roller 66 is provided in a fixed position about the cage and is configured to receive the blade mounting means 22 through the center of its diameter. This blade roller 66 has a larger diameter than rollers 54 and 56 to provide the necessary clearance for receiving the blade holding means 22. The rollers 54 and 56 and blade roller 66 extend outside the periphery of cage 52 so that such rollers contact the inner cam surface 48 and bottom bearing ring surface 42, thereby allowing the roller cage assembly 20 to rotate freely within cam 18.

The roller cage assembly is held in place within the ring 16 by use of a locking ring 24 which is threadably received within the top portion of ring 16. The locking ring 24 is provided with two indentations 70 in its top surface which can receive a spanner tool (not shown) for installing and removing the locking ring 24 from the adjustment ring 16.

The blade mounting means 22 includes a body 74 having an externally threaded portion 76 extending up through a spacer member 78 provided in blade roller 66. The blade body 74 is secured to the roller cage 52 by an internally threaded collar 80 received on the externally threaded portion 76 of blade body 74. The threaded collar also has an externally threaded portion 82 on its upper end. An axially moveable center rod 84 is positioned within body 74 and has an externally threaded portion 86 at its uppermost or distal end from body 74 extending above the threaded collar 80. A blade holder 88 carrying the diamond tipped cutting blade 30 is positioned within body 74 and is secured to the lowermost or proximal end of center rod 84. A drive pin 90 is threaded through the body 74 and is received in a slot 92 provided in center rod 84 to prevent rotational movement of rod 84 while allowing for axial movement of rod 84 so that the cutting blade 30 can be raised and lowered relative to the roller cage assembly 20 and base 14.

A thimble 96 having a knurled outer surface 98 is threaded onto the externally threaded portions 82 and 86 of threaded collar 80 and center rod 84, respectively. The thimble 96 is provided with two internally threaded portions 100 and 102 for receiving such externally threaded portions 82 and 86, respectively. Such an arrangement has been called a "micrometer" thread or a "differential" thread arrangement to allow for precise axial movement of the center rod upon rotational movement of the thimble. The center rod 84 is prevented from being unscrewed from the thimble 96 by use of a retaining screw 104.

By way of example, the internal thread 100 of thimble 96 and the external thread 82 of collar 80 are a metric 5 mm diameter and having a pitch of 0.5. The internal thread 102 of thimble 96 and the external thread 86 of rod 84 are a metric 3.5 mm diameter and having a pitch of 0.6. Therefore, upon clockwise rotation of the roller cage assembly 20 within the trephine 10 but not allowing the thimble 96 itself to turn in the operator's fingers, the center rod 84 and consequently, the blade holder 88 and diamond tipped blade 30 will lowered by 0.096 mm per revolution of the roller cage assembly 20.

The blade mounting mechanism 22 is positioned through the roller cage assembly 20 on an angle to allow for maximum viewing by the surgeon through the center of the device. The blade holder 88 is angled with respect to the center rod 84 so as to present the cutting blade 30 in a vertical orientation to the corneal tissue E to be cut by the trephine. By way of the specific example above, the 0.096 mm of axial movement per revolution of the roller cage assembly 20 will translate into 0.1 mm movement of the blade 30 into the corneal tissue.

The roller cage assembly 20 freely rotates within cam 18 of trephine 10 on spring loaded rollers 54 and 56 and the blade roller 66. Since the spring loaded rollers are biased radially outwardly at all times, these rollers force the blade roller 66 to closely follow the inner surface 48 of cam 18. As is shown in FIGS. 4 and 5, it is possible for the inner cam surface to be of various diameter round configurations as shown at 46 in FIG. 4 or to be of an other than round or possibly oval configuration as shown at 48 in FIGS. 2 and 5. In this fashion the blade mounting means 22 and cutting blade 30 will closely follow the geometric pattern provided on the inside surface of cam 18.

Suction ring 12 of trephine 10 functions by virtue of the void space left between inner and outer suction rings 108 and 110, which void space communicates with a tube 112 adapted to be connected to a source of suction. Suction ring 12 may be identical to the one provided in the cutting device disclosed in the aforementioned U.S. Pat. No. 4,423,728, and accordingly may have a frustoconical shape with a constant height throughout. It is also contemplated that the suction ring may be slightly tilted in such a way that its height varies between maximum and minimum values at about 180° opposed locations in order to compensate for the variation in corneal thickness between the inferior (minimum corneal thickness) and superior (maximum corneal thickness) cornea.

The various included pieces and parts of which trephine 10 is comprised may be prepared by conventional methods, for example casting, machining, etc., from a suitable metal or metal alloy (e.g. stainless steel). Alternatively, injection molded plastic pieces and parts may be utilized in a disposable embodiment of the invention.

The operation of trephine 10 will be described with reference to an ophthalmic surgical procedure for removing a piece of corneal tissue in contemplation of a corneal transplant operation. First, the surgeon or operator would grasp the trephine 10 by finger grips 26 and place the suction ring upon the corneal surface E of the eye. An appropriate suction would be applied to suction ring 12 to secure the trephine 10 to the corneal surface. To start an incision, the operator would first rotate the thimble 96 clockwise to its lowest position which would raise the cutting blade 30 to its fully up position. Then, by rotation of course adjustment ring 16, the operator would lower the blade mounting means 22 and diamond tipped blade 30 to a position immediately adjacent to the corneal tissue E. The locking screw 38 would then be secured to prevent further rotation of the adjusting ring 16.

The operator would then grasp the thimble 96 firmly within the fingers of his or her other hand and rotate the roller cage assembly 20 in a clockwise direction about the annular base 14 without allowing the thimble 96 to rotate. Consequently, the blade 30 would be lowered into the corneal tissue 0.1 mm per revolution of the roller cage assembly 20 until the corneal tissue E has been completely dissected. In this manner, the cutting blade 30 of the trephine 10 provides a continuous cutting action of the tissue providing a smooth annular hole therein. To raise the cutting blade 96, the operator would rotate thimble 30 clockwise while holding the roller cage assembly 20 still until the thimble 96 is screwed back down against the roller cage member 52 which would raise the blade 30 back to its original position.

To change from one interchangeable cam 18 to another, the operator would unscrew the locking ring 24 with spanner wrench (not shown). The roller cage assembly 20 would then be removed from the course adjustment ring 16 and set aside. The adjustment ring 16 would then be removed from the annular base 14. The retaining screw (not shown) in the side of ring 16 would be loosened and cam 18 would be removed from the ring 16. A different cam having a different inside dimension could be put back into the ring 16 and the steps outlined above reversed to place the trephine 10 back in working condition.

Thus, the cam-guided trephine in accordance with the present invention provides a technique for allowing a vertically disposed blade 30 to provide an annular cut of essentially any practical shape, diameter and depth. However, it should be noted that while a vertical blade 30 has been shown in use, it would be equally possible to utilize an angled blade to be used in its place. And, although the trephine in accordance with the present invention is disclosed for use in a procedure for a corneal keratoplasty operation, it will be readily apparent to those skilled in the art that other surgical procedures may be performed by the present invention as well.

Although the present invention has been described with respect to a specific embodiment of the apparatus, it is also readily, apparent that modifications, alterations, or changes may be made without departing from the spirit and scope of the invention as defined by the following claims.

What is claimed is:

1. An ophthalmic device having a cutting blade for cutting a selected portion of an eye, said ophthalmic device comprising:
   a base;
   a means to conform and secure said ophthalmic device to said eye, said means to conform and secure being mounted on said base;
   an adjustment ring movably disposed on said base, said adjustment ring providing a predetermined gross position adjustment of said cutting blade relative to said eye;
   an interchangeable cam mounted on said adjustment ring, said interchangeable cam defining an interior cam surface having a predetermined shape;
   a roller cage having at least two support rollers positioned about and extending beyond a periphery of said roller cage, said roller cage being positioned within said interchangeable cam, said support rollers being spring-biased radially outwardly relative to said roller cage, said roller cage further comprising a blade roller positioned at and extending beyond said periphery of said roller cage, whereby said support rollers and said blade roller contact and follow said interior cam surface upon rotation of said roller cage relative to said cam; and
   a blade mounting means mounted axially on said blade roller, said cutting blade being mounted on said blade mounting means, and said blade mounting means comprising a differential thread mechanism, whereby said differential thread mechanism causes said cutting blade to move a predetermined distance relative to said eye upon each revolution of said roller cage about said interior cam surface, and whereby said cutting blade is moved in a path determined by said predetermined shape of said interior cam surface.

2. An ophthalmic device in accordance with claim 1, wherein said interior cam surface has a substantially circular shape.

3. An ophthalmic device in accordance with claim 1, wherein said interior cam surface has a non-circular shape.

4. An ophthalmic device in accordance with claim 1, wherein said differential thread mechanism provides for about 0.1 mm of movement of said cutting blade relative to said eye upon each revolution of said roller cage about said interior cam surface.

5. An ophthalmic device in accordance with claim 1, wherein said base comprises a generally annular upper section and a distally-tapering cone-shaped section, said distally-tapering cone-shaped section having a proximal portion adjacent said generally annular upper section and a distal portion spaced from said generally annular upper section, and wherein said means to conform and secure comprises a suction apparatus adapted to be placed on said eye and substantially fixed thereto by means of suction, said suction apparatus being mounted on said distal section of said distally-tapering cone-shaped section.

6. An ophthalmic device in accordance with claim 1, wherein said adjustment ring is threadably disposed on said base, whereby rotation of said adjustment ring relative to said base causes said cutting blade to move relative to said eye.

7. An ophthalmic device in accordance with claim 1, said ophthalmic device further comprising a finger grip section mounted on said base, said finger grip section being angled upwardly relative to said base.

8. An ophthalmic device having a cutting blade for cutting a selected portion of an eye, said ophthalmic device comprising:
   a base;
   a cam mounted on said base, said cam defining an interior cam surface having a predetermined shape;
   a roller cage having a plurality of support rollers positioned about and extending beyond a periphery of said roller cage, said roller cage being positioned within said cam, said support rollers being spring-biased radially outwardly relative to said roller cage, said roller cage further comprising a blade roller positioned at and extending beyond said periphery of said roller cage, whereby said support rollers and said blade roller contact and follow said interior cam surface upon rotation of said roller cage relative to said cam; and
   a blade mounting means axially mounted on said blade roller, said blade mounting means being constructed to retain said cutting blade, whereby said cutting blade is moved in a path determined by said predetermined shape of said interior cam surface.

9. An ophthalmic device in accordance with claim 8, said ophthalmic device further comprising a course adjustment ring mounted on said base, said cam being mounted on said course adjustment ring, whereby said course adjustment ring provides a predetermined gross position adjustment of said cutting blade relative to said eye.

10. An ophthalmic device in accordance with claim 8, wherein said blade mounting means further comprises a differential thread mechanism, whereby said differential thread mechanism causes said cutting blade move a predetermined distance relative to said eye upon revolution of said roller cage about said interior cam surface.

11. An ophthalmic device in accordance with claim 10, wherein said predetermined distance of movement of said cutting blade relative to said eye is 0.1 mm.

12. An ophthalmic device in accordance with claim 8, said device further comprising a means to conform and secure said ophthalmic device to said eye.

13. An ophthalmic device in accordance with claim 8, wherein said interior cam surface is substantially circular.

14. An ophthalmic device in accordance with claim 8, wherein said interior cam surface is non-circular.

15. An ophthalmic device having a cutting blade for cutting a selected portion of an eye, said ophthalmic device comprising:

a base;

a cam mounted on said base, said cam defining an interior cam surface having a predetermined shape;

a roller cage having a plurality of support rollers positioned about and extending beyond a periphery of said roller cage, said roller cage being positioned within said cam, said support rollers being spring-biased radially outwardly relative to said roller cage, said roller cage further comprising a blade roller positioned at and extending beyond said periphery of said roller cage, whereby said support rollers and said blade roller contact and follow said interior cam surface upon rotation of said roller cage relative to said cam; and a blade mounting means mounted axially on said blade roller, said cutting blade being mounted on said blade mounting means, and said blade mounting means comprising a differential thread mechanism, whereby said differential thread mechanism causes said cutting blade to move a predetermined distance relative to said eye upon each revolution of said roller cage about said interior cam surface, and whereby said cutting blade is moved in a path determined by said predetermined shape of said interior cam surface.

16. An ophthalmic device in accordance with claim 15, wherein said interior cam surface is substantially circular.

17. An ophthalmic device in accordance with claim 15, wherein said interior cam surface is non-circular.

18. An ophthalmic device in accordance with claim 15, said ophthalmic device further comprising a course adjustment ring mounted on said base, said cam being positioned on said course adjustment ring, whereby said course adjustment ring provides a predetermined gross adjustment of said cutting blade relative to said eye.

* * * * *